United States Patent [19]
Bollé

[11] Patent Number: 5,138,723
[45] Date of Patent: Aug. 18, 1992

[54] GOGGLES WITH HORIZONTALLY PROJECTING NOSE OPENING

[75] Inventor: Maurice Bollé, Oyonnax, France

[73] Assignee: Establissements Bollé S.N.C., Oyonnax, France

[21] Appl. No.: 653,073

[22] Filed: Feb. 7, 1991

[51] Int. Cl.⁵ ............................... A61F 9/02
[52] U.S. Cl. ........................... 2/430; 2/432; 2/439; 2/447
[58] Field of Search .................. 2/428, 430, 436, 439, 2/440, 445, 446, 447, 431, 442, 454; 351/61, 83, 90, 99, 101

[56] References Cited

U.S. PATENT DOCUMENTS

| | | | |
|---|---|---|---|
| 2,617,100 | 11/1952 | Moeller | 2/447 |
| 3,517,393 | 6/1970 | Beauchef | 2/436 |
| 3,531,189 | 9/1970 | Petito | 351/90 |
| 3,614,216 | 10/1971 | Rosenthal | 351/44 |
| 3,945,044 | 3/1976 | McGee et al. | 2/436 |
| 4,621,378 | 11/1986 | Hatchman | 2/431 |
| 4,707,863 | 11/1987 | McNeal | 2/436 |
| 5,012,527 | 5/1991 | Michel | 2/9 |

FOREIGN PATENT DOCUMENTS

| | | | |
|---|---|---|---|
| 2448842 | 4/1976 | Fed. Rep. of Germany | 351/90 |
| 1378839 | 3/1988 | U.S.S.R. | 2/454 |
| 577153 | 5/1946 | United Kingdom | 2/439 |
| 2199155 | 6/1988 | United Kingdom | 351/90 |

*Primary Examiner*—Werner H. Schroeder
*Assistant Examiner*—Michael A. Neas
*Attorney, Agent, or Firm*—Gregg I. Anderson

[57] ABSTRACT

A goggle including a unitary lens mountable about the head of a user is shown. A lens of the goggle is mounted in a frame. The lens has no nose opening and projects from near the forehead to the tip of the nose of the user. The frame of the goggle has a lower half which projects forwardly and has a nose opening in a horizontal plane to fit about the nose. Second or bottom lenses positioned in the lower half of the frame allow downward vision of the user.

22 Claims, 2 Drawing Sheets

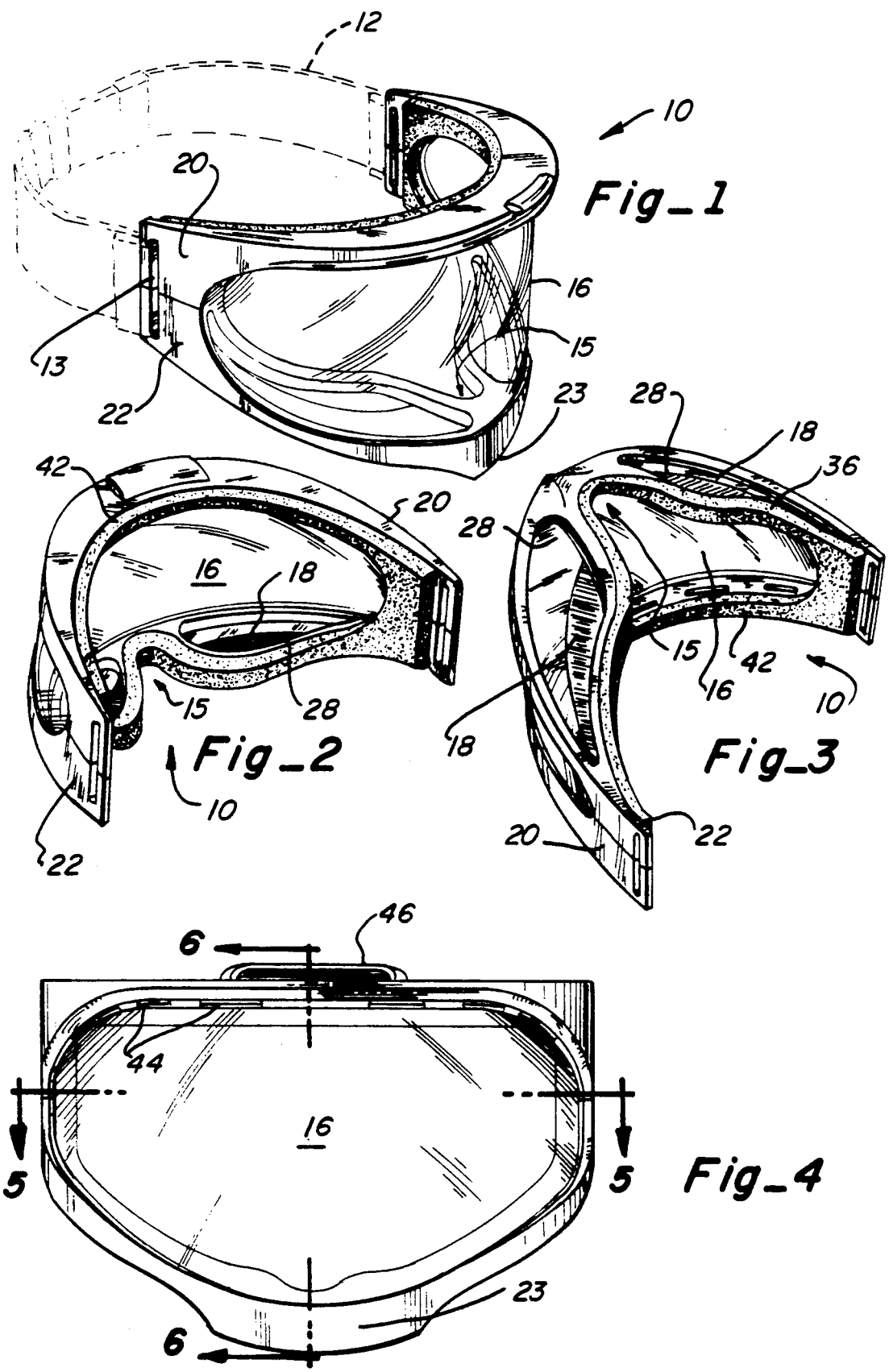

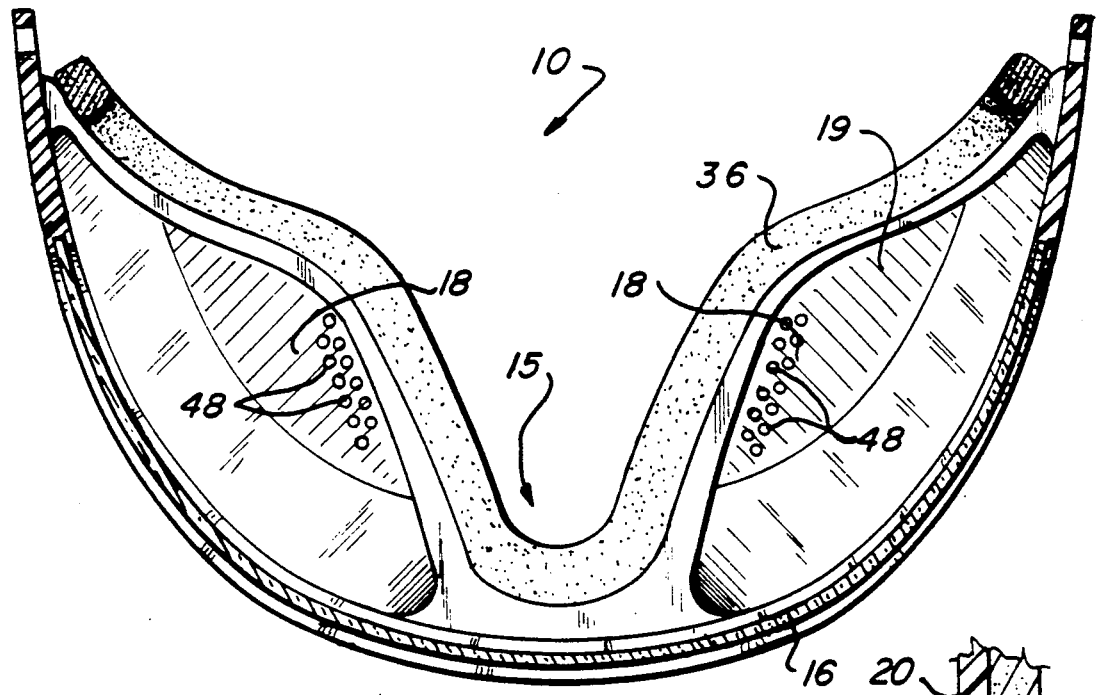
Fig_5
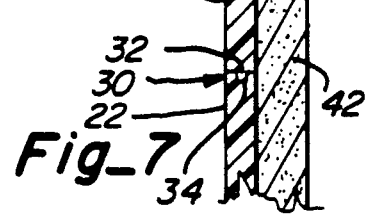
Fig_7
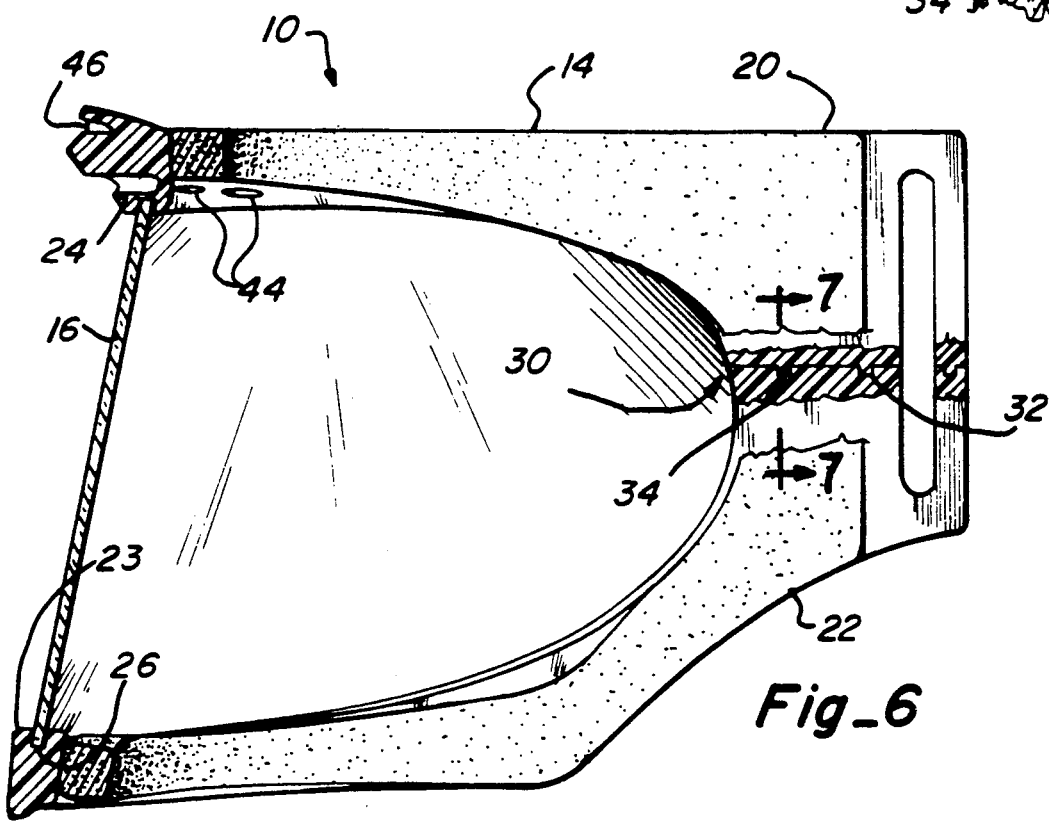
Fig_6

GOGGLES WITH HORIZONTALLY PROJECTING NOSE OPENING

BACKGROUND OF THE INVENTION

1. Field of the Invention

The present invention relates generally to goggles to fit about the head and cover a portion of the face and the eyes of a wearer or user. More particularly, the present invention relates to goggles adapted for use in snow skiing.

2. Description of the Prior Art

Various forms of goggles have existed and been proposed over the years to protect the face and eyes. Goggles have gained widespread acceptance for use in the sport of snow skiing. In virtually all of the prior art a front lens mounted in a frame extends from one terminal end of the frame to another terminal end, partially wrapping around and covering the face of the user, completely covering the eyes. The frame, and the connected lens, typically have a nosepiece opening formed therein. The nosepiece opening allows the frame and lens to rest on the nose. The nosepiece opening is generally in a vertical plane substantially parallel to a plane containing the lens and the face of the user of the goggle. The nosepiece includes padding and is typically opaque. Some obstruction of the user's forward vision is inherent. Prior art nosepieces therefore add an additional blind spot to the wearer. In addition, the tip of the nose of the wearer or user is left unprotected.

SUMMARY OF THE INVENTION

A goggle includes a frame having a nosepiece opening that projects forwardly to surround the nose of a user in a horizontal plane. A first lens is mounted in the frame. The lens projects at an angle from near the forehead forwardly away from the forehead to the tip of the nose of the wearer. The lens extends continuously from one terminal end of the frame, at a side or temple area of the goggle, to another terminal end at the opposite temple of the user or wearer.

Second or auxiliary lenses, one for each eye, are connected to openings formed in the frame. The openings project forwardly and lie in the substantially horizontal plane, providing downward vision for the user, which would otherwise not be available.

The goggle therefore provides significant peripheral vision plus enhanced forward vision because of removal of the conventional type nosepiece. An added benefit of greater face coverage is also realized.

Other aspects, features and details of the present invention can be more completely understood by reference to the following detailed description of the preferred embodiment, taken in conjunction with the drawings, and from the appended claims.

BRIEF DESCRIPTION OF THE DRAWINGS

FIG. 1 is a perspective view of goggles of the present invention, a strap for holding the goggles about a head of a user shown in phantom line.

FIG. 2 is a rear perspective view of the goggles shown in FIG. 1.

FIG. 3 is a bottom perspective view of the goggles shown in FIG. 1.

FIG. 4 is a front elevational view of the goggles shown in FIG. 1.

FIG. 5 is a sectional view taken in the plane of line 5—5 of FIG. 4.

FIG. 6 is a sectional view taken in the plane of line 6—6 of FIG. 4.

FIG. 7 is an enlarged fragmentary sectional view taken in the plane of line 7—7 of FIG. 6.

DETAILED DESCRIPTION OF THE PREFERRED EMBODIMENT

A goggle 10 is shown in FIGS. 1-4. The goggle 10 is adapted particularly to fit about the head of a wearer or user. The goggle 10 is held in place by a flexible elastic strap 12. The goggle 10 covers the eyes and wraps about a portion of the face, completely covering the eyes of the user. The face and eyes are protected from wind and cold.

The goggle 10 includes a frame 14 made of polyurethane or some other flexible material. The frame 14 has a clear plastic first lens 16 of acetate, polycarbonate or like light flexible clear plastic material mounted therein. As is known in the art, the lens 16 is permanently connected to the frame 14 or, using snap connections between the lens 16 and the frame 14, releasably connected to the frame 14. The releasable connection allows the user to exchange lenses depending on the weather conditions. The frame 14 includes a forward nose opening 15 as contrasted to the prior art, lies in a substantially horizontal plane to wrap around the nose of the user. The horizontal plane is generally perpendicular to the lens 16 at the connection between the lens 16 and the frame 14. The prior art nosepiece openings lie substantially in a plane generally parallel to the lens and the nosepiece actually rests on the nose.

The frame 14 also includes openings 28 for second bottom lenses 18. The bottom lenses 18 are in the same horizontal plane as the nose opening 15. The bottom lenses 18 give a downward field of vision to each eye of the user of the goggle 10 that would not be available with the projecting frame 14.

The frame 14 includes an upper half 20 and a lower half 22. Where the halves 20 and 22 join, a strap opening 13 is defined for connection of the frame 14 to the strap 12. The lower half 22 includes a depending noseguard 23 which protects the tip of the nose and is formed integrally with the lower half 22 immediately forward of the nose opening 15.

A connection 30 (FIG. 7) holds the upper and lower frame halves 20 and 22 together. As shown, the connection 30 is a tongue and groove type connection. A tab 32 on the upper half 20 connects into a connection slot 34 on the lower half 22. The connection 30 could be by any of several other conventional means as well. Adhesive bonding, heat welding or any other connection procedure may be used to enhance the bond between the frame halves 20 and 22 at the connection 30.

The front lens 16 is interconnected between the upper and lower frame halves 20 and 22. As shown, the lens 16 fits into an upper lens groove 24 and a lower lens groove 26 of the frame halves 20 and 22 (FIG. 6). When connected between the upper and lower frame halves 20 and 22, the lens 16 projects forwardly from near the forehead of the wearer to the tip of the nose. A substantially straight line is defined in any vertical plane through the lens 16, end points of the line being generally the forehead and the tip of the user's nose.

The lens 16 is initially cut or formed from a cylindrical section of clear plastic material. The cylindrical section is bent about a vertical axis to fit into the frame 14. The lens 16 continuously curves from one terminal end of the frame 14 to the other (FIG. 5). The lens 16 can also be formed from a conical section.

Grooves, not specifically shown, receive peripheral edges of the second bottom lens 18 for connection to the bottom half of the frame 22 within the openings 28. Again a permanent or releasable connection between the lenses 18 and the frame 14 is available. In most instances a permanent connection is adequate and problems with glare can be diminished by blanking or tinting so as to make opaque a portion 19 (FIG. 5) of the lenses 18.

Around the nose opening 15, a foam pad is connected to the lower frame half 22. The foam pad 36 is connected in a conventional manner well known in the manufacture of ski goggles. The foam pad 36 defines a soft layer for contact with the nose and cheeks of the user.

The upper frame 20 includes vents 44 for ventilating the interior of the goggle 10 and removing condensation from the lens 16. A large central vent 46 allows for a larger volume of air to enter the interior of the goggle 10. Additional lower vents vent holes 48 (FIG. 5) provide continuous through circulation to remove condensation from the lenses 16 and 18 of the goggle 10.

The goggle 10 thus includes a unique forwardly projecting nose opening 15 to protect the nose and to allow greater visibility to the user than a conventional nosepiece, which rests on the nose. Downward visibility is enhanced by the bottom lenses 18. The cylindrical shape from which the front lens 16 is formed, is adjusted in connection to the frame 14 into a conical shape, projecting forwardly from the forehead to the tip of the nose. Alternatively, the lens 16 may be formed in a conical shape originally. Ventilation is provided to remove condensation from the interior of the goggle 10.

Although the present invention has been described with a certain degree of particularity, it is understood that the present disclosure has been made by way of example, and changes in detail or structure may be made without departing from the spirit of the invention, as defined in the appended claims.

I claim:

1. A goggle for connection about a head and over the eyes of a user, comprising in combination:
   a frame having a curved surface including a nose opening projecting forwardly in a generally horizontal plane around the nose of the user; and
   a first lens connected to said frame and continuously curving from one terminal end of the frame to another, whereby the eyes of the user are unobstructed by the frame.

2. The invention as defined in claim 1 further including a second lens mounted in said frame adjacent said nose opening and substantially in said horizontal plane, whereby the second lens provides downward vision for said user.

3. The invention as defined in claim 2 wherein said second lens includes an opaque portion to control glare.

4. The invention as defined in claim 1 including means for venting air into the goggle.

5. The invention as defined in claim 1 wherein said frame includes a foam layer intermediate said frame and the face of said user.

6. The invention as defined in claim 1 wherein said frame comprises two pieces having grooves formed therein to hold said first lens.

7. The invention as defined in claim 1 wherein said lens is formed from a cylindrical section.

8. The invention as defined in claim 1 wherein said lens is formed from a conical section.

9. The invention as defined in claim 1 wherein said first lens projects forwardly from the forehead of the user to the tip of the nose of the user along a substantially straight line in any vertical plane through said lens.

10. A goggle for connection about a head and over the eyes of the user, comprising in combination:
    a frame including a nose opening projecting forwardly in a generally horizontal plane around the nose of the user;
    a first lens mounted in said frame extending continuously from one terminal end of the frame to another, whereby the eyes of the user are unobstructed by the frame; and
    a second lens mounted in said frame adjacent said nose opening and substantially in said horizontal plane, whereby the second lens provides downward vision for the eyes of said user.

11. The invention as defined in claim 10 wherein said second lens includes an opaque portion to control glare.

12. The invention as defined in claim 10 including means for venting air into the goggle.

13. The invention as defined in claim 12 wherein said venting means comprises an opening in said frame.

14. The invention as defined in claim 12 wherein said second lens includes holes formed therein.

15. The invention as defined in claim 10 wherein said frame includes a foam layer intermediate said frame and the face of said user.

16. The invention as defined in claim 10 wherein said frame comprises two pieces having grooves formed therein to hold said first lens.

17. The invention as defined in claim 10 wherein said lens is formed from a cylindrical section.

18. The invention as defined in claim 10 wherein said lens is formed from a conical section.

19. The invention as defined in claim 10 wherein said lens projects forwardly from the forehead of the user to the tip of the nose of the user.

20. A goggle for connection about a head and over the eyes of a user, comprising in combination:
    a frame including a nose opening projecting forwardly in a generally horizontal plane around the nose of the user;
    a first lens extending continuously from one terminal end of the frame to another, whereby the eyes of the user are unobstructed by the frame; and
    a second lens mounted in said frame adjacent said nose opening and substantially in said horizontal plane, whereby the second lens provides downward vision for said user.

21. The invention as defined in claim 20 wherein said second lens includes an opaque portion to control glare.

22. The invention as defined in claim 20 wherein said second lens includes vent holes formed therein.

* * * * *